US010071176B2

(12) United States Patent
Duvoisin et al.

(10) Patent No.: US 10,071,176 B2
(45) Date of Patent: Sep. 11, 2018

(54) DISINFECTION COMPOSITION, DISINFECTION METHOD, DISINFECTION PROTOCOL FOR TOOTH BRUSHES, AND DISINFECTION PRODUCT

(71) Applicant: Charles Adriano Duvoisin, Balneário Camboriú (BR)

(72) Inventors: Charles Adriano Duvoisin, Balneário Camboriú (BR); Frank Bollmann, São Bento do Sul (BR)

(73) Assignee: Charles Adriano Duvoisin, Balneário Camboriú (BR)

( * ) Notice: Subject to any disclaimer, the term of this patent is extended or adjusted under 35 U.S.C. 154(b) by 0 days.

(21) Appl. No.: 15/039,250

(22) PCT Filed: Nov. 27, 2014

(86) PCT No.: PCT/BR2014/000423
§ 371 (c)(1),
(2) Date: Jun. 30, 2016

(87) PCT Pub. No.: WO2015/077857
PCT Pub. Date: Jun. 4, 2015

(65) Prior Publication Data
US 2017/0021044 A1  Jan. 26, 2017

(30) Foreign Application Priority Data

Nov. 28, 2013 (BR) .............................. 102013030653

(51) Int. Cl.
| | | |
|---|---|---|
| *A61L 2/18* | (2006.01) | |
| *A01N 25/02* | (2006.01) | |
| *A01N 25/30* | (2006.01) | |
| *A01N 47/44* | (2006.01) | |
| *B08B 3/04* | (2006.01) | |
| *B08B 3/08* | (2006.01) | |
| *C11D 3/26* | (2006.01) | |

(52) U.S. Cl.
CPC ................ *A61L 2/18* (2013.01); *A01N 25/02* (2013.01); *A01N 47/44* (2013.01); *B08B 3/08* (2013.01); *A61L 2202/17* (2013.01)

(58) Field of Classification Search
CPC ....... A61L 2/18; A61L 2202/17; A01N 25/02; A01N 25/30; A01N 47/44; B08B 3/04; B08B 3/08; C11D 1/662; C11D 3/2065; C11D 3/26
See application file for complete search history.

(56) References Cited

U.S. PATENT DOCUMENTS

| | | |
|---|---|---|
| 4,748,158 A | 5/1988 | Biermann et al. |
| 4,920,100 A | 4/1990 | Lehmann et al. |
| 2015/0374866 A1* | 12/2015 | Fischer ................. A61Q 11/02 422/28 |

FOREIGN PATENT DOCUMENTS

| | | | |
|---|---|---|---|
| BR | PI0514935-5 A | 7/2008 | |
| BR | PI0702469-0 A2 | 3/2009 | |
| CH | 700343 B1 | 8/2010 | |
| CN | 103314993 A | 9/2013 | |
| DE | 20304504 U1 | 4/2004 | |
| KR | 20080049158 A | 6/2008 | |
| WO | 2009105845 A2 | 9/2009 | |
| WO | 2009117299 A2 | 9/2009 | |
| WO | WO 2009/117299 * | 9/2009 | ............. C11D 1/835 |
| WO | 2010010345 A2 | 1/2010 | |
| WO | 2012034032 A2 | 3/2012 | |

OTHER PUBLICATIONS

Menolli, RA. et al.: "Microbiological Contamination of Toothbrushes and Identification of a Decontamination Protocol Using Chlorhexidine Spray", Rev. Odonto. Cienc. 2012, 27(3), pp. 213-227.
Eshwar, S. et al: "How Clean Is the Toothbrush That Cleans Your Tooth?", Int. J. Dent. Hygiene. 7, 2009, pp. 237-240.
Decker, E.M. et al.: "Effect of Xylitol/Chlorhexidine Versus Xylitol or Chlorhexidine as Single Rinses on Initial Biofilm Formation of Cariogenic *Streptococci*", Quintessence Int. 2008, 39(1), pp. 17-22.
Filho, P. N.: "Microbial Contamination of Tooth-Brushes and Their Decontamination", Pediatric Dentistry—22:5, 2000, pp. 381-384.
PCT International Search Report dated Feb. 26, 2015 from corresponding Application No. PCT/BR2014/000423.
PCT International Search Report dated Feb. 26, 2015 from corresponding Application No. PCT/BR2014/000422.

* cited by examiner

*Primary Examiner* — Brian P Mruk
(74) *Attorney, Agent, or Firm* — Dilworth IP, LLC

(57) ABSTRACT

The present invention relates to a disinfection composition, particularly for lasting disinfection of synthetic fibres, synthetic surfaces, metallic surfaces and composite surfaces, and similar surfaces, said disinfection composition comprising at least one disinfectant, at least one fat- and residue-removing component, at least one additional protection component and additional components which are compatible with the above components and have low or no toxicity. The invention further relates to a disinfection method, to a specific tooth brush disinfection protocol and finally, to a corresponding disinfection product.

13 Claims, No Drawings

DISINFECTION COMPOSITION, DISINFECTION METHOD, DISINFECTION PROTOCOL FOR TOOTH BRUSHES, AND DISINFECTION PRODUCT

FIELD OF APPLICATION

The present invention relates to the field of chemical industry, notably to the chemical preparations industry for medical, dental and hygienic purposes.

INTRODUCTION

The present invention relates to a disinfection composition based on chlorhexidine, cationic and/or non-ionic surfactants and xylitol, for lasting disinfection of synthetic fibers, synthetic surfaces, metal surfaces and composite surfaces, and the like. In addition, the present invention relates to a disinfection method of surfaces, a disinfection protocol of toothbrushes and, finally, to a disinfection product.

STATE OF THE ART

The use of chlorhexidine in disinfection liquid compositions is long known in the state of the art, as demonstrated by, for example, the German patent document DE 203 04 504, disclosing a toothbrush-cleaning composition wherein it comprises cetylpyridinium chloride and/or a mixture of chlorhexidine (including derivatives), optionally comprising dyes and various fragrances and/or plant extracts. Said German document, even though describing a chlorhexidine-based product for cleaning bristles of toothbrushes, neither mentions the time of residual action of the product on the toothbrush after separating it from the bristles, nor refers to the intended disinfection characteristics. There is no mention as to how the proposed composition acts, or to the success of the removal of various residues to which toothbrushes, for instance, are exposed to daily.

Patent document CH 700 343 discloses a care solution for toothbrushes, specifically intended for the cleaning of bristles of toothbrushes by dipping them in the solution. Said composition can comprise from 80 to 90 wt % vegetable glycerin, from 4 to 10 wt % demineralized water, from 1.00 to 1.40 wt % chlorhexidine digluconate, from 2.0 to 5.0 wt % rosemary extract, from 2.0 to 5.0 wt % mint extract. Just like said German document, CH 700 343 neither mentions the time of residual action of the product on the toothbrush after the separation from the bristles, nor refers to the intended disinfection characteristics. There is no mention as to how the proposed composition acts, or to the success of the removal of various residues to which toothbrushes, for instance, are exposed to daily.

As for Brazilian patent document PI 0702469-0, it discloses formulation of antiseptic solution for application in dentistry to prevent dental caries and further oral diseases. Even though said formulation exhibits antiseptic solutions containing, among other things, guanidines and biguanidines, surfactants, solvents etc., it is intended specifically to the hygiene of the oral cavity, thus having no reference to its use as a disinfection agent for bristles or other external elements. Again, there is a lack of references as to the time of residual action of the product on the toothbrush after the separation from the bristles and to intended disinfection characteristics. Also, since it is a mouthwash, there is no mention as to how the proposed composition acts, or to the success of the removal of various residues to which toothbrushes, for instance, are exposed to daily.

The combined use of chlorhexidine and alkylpolyglycosides in antimicrobial compositions is also known in the state of the art, as demonstrated by document WO 2012/034032, which discloses antimicrobial solutions that in certain cases comprise a biguanide and at least one alkylpolyglucoside. The solutions and methods proposed by this document are intended for the elimination or reduction of bacteria, fungi and viruses from the surfaces, for example, of medical equipment, organic surfaces like the skin and sutures, and other inorganic surfaces. There is no mention to the specific treatment of surfaces with the characteristics of toothbrush bristles, as well as there is no mention to the time of residual action of the product on toothbrush bristles, for example, after it is separated from the bristles.

Another example of the combined use of chlorhexidine and cationic detergents such as alkylpolyglucosides is given by the sanitizing compositions and methods of WO/010345 2010, which discloses sanitizing compositions for use in combination with specific cleaning compositions. In addition to requiring specific protocols for each type of surface to be disinfected, said document does not mention the specific treatment of surfaces with characteristics similar to those of toothbrush bristles.

Document WO 2009/117299 discloses chlorhexidine-based cleaning, disinfecting, sanitizing and sterilizing preparations and non-ionic surfactants, however, exhibiting the same deficiencies of above-mentioned document WO 2010/010345. The same deficiency occurs with the composition of personal and domestic hygiene disclosed by document PI 0514935-5.

As can be inferred from the above description, there is room for improvements in formulations of disinfection compositions for lasting disinfecting of synthetic fibers, synthetic surfaces, metal surfaces, composite surfaces, similar surfaces and the like.

In addition to the compositions and combinations disclosed by the above-mentioned documents, it is also worth mentioning some products that are known in the state of the art and that are also used, both alone and in compositions, as main active principle or as a complement, as compositions for oral hygiene and, eventually, cited for disinfection of surfaces.

One such product that is worth mentioning is triclosan (in Portuguese, also known as triclosano), also widely used in dentrifices, which disrupts the bacterial cell membrane, inhibiting its enzymatic function (Torres C R G, Kubo C H, Anido A A, Rodrigues J R. *Agentes antimicrobianos e seu potencial de use na Odontologia. Pós Grad Rev Fac Odontol São José dos Campos* 2000:3:43-52.). At low concentrations, there is adsorption of microorganisms in the lipid moiety, which causes a drastic change in cellular transport and thereby prevents proper metabolism and cell reproduction, and, accordingly, providing a broad spectrum antimicrobial effect. Despite being a chemical agent capable of providing bacteriostatic action, its anionic charge causes it to have a low substantiality. Its main drawback is the fact that it is anionic, unlike, for example, chlorhexidine and cetylpyridinium chloride, which are cationic. This feature also impairs a synergy action with a cationic surfactant. In addition to being highly toxic to the human body, as well as carcinogenic and also highly polluting to the environment.

Another product widely used for disinfection is sodium hypochlorite, also known as bleach or javel water. Sodium hypochlorite is a chemical compound with the formula NaClO, typically found in liquid form, in slightly greenishyellow color, of pungent odor, water soluble, non-flammable, photosensitive (it decomposes when in direct contact with the light), corrosive to metals, having easy oxidation and decomposition, that releases toxic gases when in contact with acids obtained from the reaction of chlorine with a diluted solution of sodium hydroxide (caustic soda). Sodium hypochlorite has germicidal properties and it is widely used for the treatment and purification of water, for disinfection of vegetables and fruits, in the production of industrial disinfectants, in the treatment of swimming pools (disinfection of water), in the composition of conventional pesticides and as an agent of sterilization in the industries of beverages such as beer, wine and cola soft drinks. It is very suitable for sterilization of domestic environments such as bathrooms and kitchens (usually more susceptible to the spread of germs). It can also be used in dental care as an irrigating solution (this use is still not widespread in Brazil, and therefore many dentists use bleach). For being a strong oxidant, it must be handled with care, since the products of its oxidation are corrosive and can cause burns to the skin and eyes, especially when at high concentrations. The reaction of sodium hypochlorite with organic compounds is violent and gives rise to toxic and even carcinogenic substances. For instance, mixtures of hypochlorite and urine should be avoided, since the reaction of this compound with ammonia leads to chloramine, which is toxic to the human body. Accidents involving sodium hypochlorite can result in harmful effects to health. If inhaled, it can cause irritation to the respiratory system, causing cough and dyspnea. If ingested, it causes bloody vomiting, nausea and diarrhea, ulcerations in the esophagus and stomach, in addition to the fact that high concentrations of sodium in the body can lead to dehydration.

On the other hand, glutaraldehyde has an environmental toxicity above 0.2 ppm/m$^3$, also being a carcinogen. It is widely used as a sterilizer and disinfectant for surgical and dental instruments, thermometers, plastic or rubber equipment, veterinary clinics and hospitals (place of consultations and surgeries); various facilities and other materials that cannot be heat sterilized, vehicles for transporting animals, feeders, waterers and eggs. Glutaraldehyde has been widely used for disinfection of certain pieces of equipment such as endoscopes, connections of medical ventilators, respiratory therapy equipment, dialyzers, spirometry tubes and others; to this end the exposure time is 30 minutes. It is not used as a surface disinfectant since it is costly and very toxic.

Finally, peracetic acid is fairly used in disinfection/sterilization of plastic, polyurethane, polyethylene, PVC, ABS, nylon 6 and 66, optical fiber, viton, silicone, natural and nitrilic rubbers, natural and synthetic fabrics. Plastics, rubber or silicone may experience dryness and/or rigidity depending on their porosity, it is highly flammable and has a strong odor. Peracetic acid (acetyl hydroperoxide or peroxyacetic acid) is a chemical product that presents itself as a colorless liquid, non-colorant, and powerful oxidizing agent with acidic pH, a density close to that of the water and slightly vinegary odor, corrosive to metals (brass, copper, galvanized iron, tin) that, at low concentration, has a fast action against all microorganisms, including bacterial spores. 0.2% peracetic acid can cause respiratory distress, its vapors are irritating, and it requires careful handling. It has low storage stability and low residual effect.

The other existing antiseptics on the market are indicated (and used), in their overwhelming majority, just as mouthwashes. The products presented and commonly used in the state of the art, either lack a disinfection power strong enough to provide an efficient hygiene of surfaces; or have said disinfection power based on highly toxic products, therefore, inappropriate for application on objects of personal use and hygiene.

Therefore, as can be inferred from the above description, there is room for improvements in formulations of disinfection compositions for lasting disinfecting of synthetic fibers, synthetic surfaces, metal surfaces, composite surfaces, similar surfaces and the like.

More specifically, there is room for sanitizing and/or hygiene compositions for objects of personal use having both combined and simultaneous antibacterial, antiseptic and deep cleaning activity with extended action especially for continuous use in toothbrush bristles, but also effective for the disinfection of other synthetic or metallic surfaces (such as, for example, oral hygiene instruments such as tongue scrapers, dental floss bow, among others, in addition to surfaces of oral devices (braces and retainers for instance), prostheses, and even hearing aids, combining minimal toxicity (to the human body) to maximum effectiveness.

The effectiveness of these compositions still lacking in the state of the art must also be extended to the complementary residues that can be found on the surfaces of objects to be disinfected, for example, fat, dentifrice debris, food debris, organic tissue, saliva, soaps, shampoos, rinses and the like, their continuous and daily use being guaranteed, without restrictions due to a toxic component or which results in human rejection.

In addition, there is room for a composition having a lasting action on the disinfected surfaces as above-mentioned and which can additionally be beneficial to the health of the user, in a complementary manner. Said composition containing, for instance, compounds having anti-caries efficacy and the like, presenting antimicrobial and also dental plaque inhibiting action, thus achieving a reduction of oral diseases and halitosis, in addition to various conditions related to medical and hearing aids.

OBJECTIVES OF THE INVENTION

One of the objectives of the present invention is the provision of a disinfection composition according to the features of claim 1. Another objective of the present invention is the provision of a disinfection method according to the features of claim 9. Another objective of the present invention is the provision of a disinfection protocol for toothbrushes according to the features of claim 10. Yet another objective of the present invention is the provision of a disinfection product according to the features of claim 11.

DETAILED DESCRIPTION OF THE INVENTION

A disinfection composition according to the invention must meet three main functions, namely:
disinfection;
removal of fat and residues; and
additional protection.
Disinfection In a preferred embodiment of the invention, the composition according to the invention has a chlorhexidine gluconate based or chlorhexidine digluconate based disinfection component or simply chlorhexidine.

Chlorhexidine has antifungal and antibacterial action, in addition to an extremely high capacity of disinfection, bacterial destruction and bacteriostatic action, thus inhibiting bacterial growth (colonies).

In the form of digluconate, it is an antimicrobial agent exhibiting disinfecting and sanitizing features. It is effective against *Salmonella* spp., *Listeria* spp., *Clostridium* spp., *E. Coli*, *Staphylococcus* spp. and *Pseudomonas* spp. (Chlorhexidine, Technical report, NEOBRAX).

Its antibacterial mechanism of action is explained by the fact that the cationic molecule of chlorhexidine is quickly attracted to the negatively charged bacterial surface and is adsorbed to the cell membrane by electrostatic interactions, presumably by hydrophobic bonds or hydrogen bridges, this adsorption being concentration-dependent. Thus, at high dosages, it causes precipitation and coagulation of cytoplasmic proteins and bacterial death; and, at lower dosages, the integrity of the cell membrane is altered, resulting in leakage of the bacterial components having low molecular weight (Hjeljord et al. 37 1973; Hugo and Longworth 38 1964; Rolla and Melsen 60 1975).

In addition, chlorhexidine is stable, is not toxic to tissues, its absorption by the mucosa and skin is minimal and it does not provoke systemic toxic side effects with extended use as well as alterations in the oral microbiota (Davies and Hull 23 1973; Case 15 1977; Rush-ton 62 1977; Winrow 73 1973; Löe et al. 45 1976).

Chlorhexidine has a substantivity (i.e., active residence time) of approximately 12 hours which is explained by its dicationic nature. Thus, a cationic end of the molecule is attached to the film, which is negatively charged, and the other cationic end is free to interact with bacteria. In this manner, it shall perform an initial bactericidal action, combined with an extended bacteriostatic action (Zanatta F B, Rösing C K. Clorexidina: *Mecanismo de ação e Evidências atuais de sua eficácia no contexto do biofilme supragengival*, Scientific-A 2007).

In addition, chlorhexidine is characterized by not developing bacterial resistance, by being non-toxic, non-corrosive and biodegradable (Chlorhexidine, Technical report, NEOBRAX).

In a preferred embodiment of the invention, the chlorhexidine content of the composition according to the invention is from 0.1 vol % to 20 vol %, preferably from 0.2 vol % to 7 vol %, more preferably from 4 vol % to 6 vol %.

Removal of Fat and Residues

Within the scope of the present invention, removal of fat and residues should be understood as the removal of complementary residues that can be found on the surfaces of objects to be disinfected, such as, for example, fat, dentifrice debris, food debris, organic tissue, saliva, soaps, shampoos, rinses and the like.

In a preferred embodiment of the invention, the composition according to the invention has a cationic surfactant as a component for fat and residues removal.

Surfactant is a substance or compound capable of reducing the surface tension of the fluid in which it is dissolved; or capable of reducing interfacial tension by preferential adsorption of a vapor-liquid interphase and another interphase.

The cationic surfactant is the one that, in aqueous solution, is ionized, thus producing positive organic ions which are responsible for the surface activity, having a positively charged radical as the hydrophilic part of the chain. That is, in this type of surfactant, it is one part of the molecule having a positive character that interacts with water, unlike the anionic surfactants. They are not compatible with anionic surfactants, forming an insoluble precipitate with them.

Cationic surfactants have germicidal properties, are provided with high bactericide power against gram-negative bacteria, as well as being fungicides, acting on certain pathogenic protozoa. They exhibit relatively low toxicity, with the absence of corrosive power (see Technical report: Amaral L et al, *Detergente doméstico, Instituto de Tecnologia do Paraná*, December 2007).

In a preferred embodiment of the invention, the composition according to the invention has a non-ionic surfactant as a component for fat and residues removal.

Non-ionic surfactants are characterized by hydrophilic groups without charges linked to the fat chain. They have as their characteristics the compatibility with most raw materials used in cosmetics, the low irritability to skin and eyes, a high power of surface and interfacial tension reduction, and low detergency and foaming powers.

In short, the surfactant decreases the surface tension of the liquid, increasing its penetration capability. It binds to and captures fat particles having lipophilic capacity and, at the other molecular end, having hydrophilicity.

In a preferred embodiment of the invention, the composition according to the invention has an alkylpolyglycoside-based fat removal component.

Alkylpolyglycosides are a family of relatively new surfactants, synthesized by reacting cornstarch glucose with a fatty alcohol. The resulting molecule is a non-ionic surfactant having good water solubility due to hydroxyl groups. Those are good detergents and have a very high degree of biodegradability. The main surfactants of this class are decyl- and lauryl-polyglucoside with a high degree of polymerization (average number of glucose units per alcohol unit).

In a preferred embodiment of the invention, the alkylpolyglycosides content of the composition according to the invention is from 0.5 vol % to 12 vol %, preferably 4 vol %.

In a preferred embodiment of the invention, said alkylpolyglycosides are decylpolyglycosides.

In another preferred embodiment of the invention, said alkylpolyglycosides are laurylpolyglycosides.

In yet another preferred embodiment of the invention, said alkylpolyglycosides are decylpolyglycosides mixed with laurylpolyglycosides.

Additional Protection

Within the scope of the present invention, additional protection should be understood as the additional protection the user is provided with against caries and oral diseases, various oral conditions and halitosis and various conditions related to medical and hearing aids.

In a preferred embodiment of the invention, the composition according to the invention has a xylitol-based additional protection component.

Xylitol is a polyalcohol having as molecular formula $C_5H_{12}O_5$ (1, 2, 3, 4, 5-pentahydroxypentane), with both inhibition and anti-adhesion actions over certain bacteria. Xylitol is transported via fructose-phosphotransferase system, resulting in intracellular accumulation of xylitol-5-phosphate. This intermediate metabolite is dephosphorylated and excreted as xylitol, without resulting in ATP production. This 'futile cycle' consumes energy and results in inhibition of bacterial growth and metabolism, particularly in some bacteria like *Streptococcus mutans, Streptococcus pneumoniae, Haemophilus influenzae*. (Pereira AFF, 2009) (Almeida LMAG).

One of the advantages of xylitol, for example over sucrose, is that, due to its high chemical and microbiological stability, it acts as a preservative of food products even at low concentrations, offering resistance to the growth of microorganisms and extending the shelf life of these products (Bar, 1991).

Since xylitol is a non-toxic substance, as classified by Food and Drug Administration (FDA) as a GRAS-type additive (Generally Regarded as Safe), its incorporation in food is legally permitted.

Acute otitis media is the second most common infection in children. It is caused by bacteria from the nasopharynx that enter the middle ear via the Eustachian tube (Erramouspe, Heyneman, 2000). According to Kontiokari et al. (1995), xylitol acts to prevent or to combat this disease, inhibiting the growth of *Streptococcus pneumoniae* bacteria, the main cause of sinusitis and middle ear infections.

When compared to other sweeteners, xylitol brings about greater benefits for oral health, preventing the incidence of cavities or reducing their formation (Mussatto S I, Roberto I C. Xilitol: *Edulcorante com efeitos benéficos para a saúde humana, Revista Brasileira de Ciências Farmacêuticas*, vol. 2002).

In a preferred embodiment of the invention, the xylitol content of the composition according to the invention is from 0.1 vol % to 30 vol %, preferably 10 vol %.

Other Components

In a preferred embodiment of the invention, the composition according to the invention comprises various additional components.

One of the additional components can be, for example, a solution of citric acid, containing 0.01 vol % to 10 vol % qs.

Other additional component can be, for example, purified water or deionized water, qsp.

Another additional component can be, for example, a pH stabilizer, in order to maintain the pH between 6.0 and 7.0 composition, in sufficient amount to meet the conditions of the composition according to the invention.

In addition to these components, preservatives, flavorings, colorings and alcohol may be part of the formulation of the composition according to the invention.

Application Forms/Pharmaceutical Forms

In a preferred embodiment of the invention, the compositions according to the invention are used in liquid form and preferably applied in the form of a immersion bath.

In another preferred embodiment of the invention, the compositions according to the invention can be used and applied respectively in the form of effervescent material (pill, tablet, powder or similar), in the form of aerosol, misting fluid, infusion fluid, vapor and other forms that are suitable for application to surfaces.

New Technical Effect

The disinfection composition according to the invention provides a unique synergy that results in a new and unique technical effect.

Initially, the composition according to the invention has high penetration power in synthetic bristles, especially toothbrush bristles. The penetration occurs even among the tufts, an effect which is primordial to the effective action of the remaining components of the formula.

As described above, this action occurs due to the reduction of the surface tension of the liquid obtained by surfactant component, being an advantage over all the liquid antiseptics on the market.

The composition according to the invention eliminates the culture existing in toothbrushes, for example, having an effective action on saliva, fat, dentifrice debris and microorganisms—components which are known to initiate the formation of a biofilm which is responsible for the culture medium.

Therefore, the composition according to the invention provides the elimination of growth and formation of colonies of microorganisms, the elimination of the medium responsible for the formation of bacterial resistance (resistant bacteria), the elimination of the potential for recontamination and/or transmission of microorganisms to the user, wherein this action is due to the combination of the ability of fat particles sequestration performed by the surfactant plus the chlorhexidine action of disinfection.

As previously mentioned, the composition according to the invention acts preventively on the inhibition of biofilm formation.

This effect is due to the action on all the components forming the biofilm and on the entire toothbrush because of the excellent penetration provided by the surfactant that, added to chlorhexidine disinfection capacity, is enhanced by the action of xylitol in inhibiting the growth and metabolism of bacteria.

The composition according to the invention acts with a disinfectant action, eliminating bacteria, fungi and viruses. The action of chlorhexidine is enhanced for the main etiological agent of dental caries, *Estreptococcus mutans*, due to combination with xylitol.

The composition according to the invention has an extended effect (continued disinfection) of at least 7 (seven) days, as a result of the combination of the effects of (i) surfactant provided with excellent penetration in the bristles and the preventive effect against the formation of biofilm, (ii) chlorhexidine disinfection capacity for bacteria, fungi and viruses, wherein chlorhexidine has its residual action of up to 12 hours (Perionews 2011) extended for at least 7 (seven) days within the composition according to the invention.

The composition according to the invention fights the action of *E. mutans* through the action enhanced by xylitol.

Therefore, it is concluded that the actions of disinfection are effective on the entire toothbrush, because of the effective permeability of liquid in addition to the capacity of deep cleaning with dissolution of the fat existing in saliva and residual organic matter.

As a result of the effects described, in addition to having a disinfected surface, there will be no residual or remaining substrate for the new formation of biofilm and proliferation of bacteria—essential and indispensable condition for high hygiene requirements.

Composition

Therefore, one objective of the present invention is the provision of a disinfection composition comprising at least one disinfection component, at least one fat removal component, at least one additional protection component and various additional components.

In a preferred embodiment of the invention, the composition according to the invention comprises:
  at least one chlorhexidine-based disinfection component;
  at least one alkylpolyglycoside-based fat removal component;
  at least one xylitol-based additional protection component;
  and one or more additional components selected from the group consisting of citric acid solution, purified or deionized water qsp, pH stabilizer, preservatives, flavorings, dyes and alcohol.

In a preferred embodiment of the invention, the composition according to the invention comprises:
  a chlorhexidine content from 0.1 vol % to 20 vol %, preferably 0.2 vol %;
  an alkylpolyglycoside content of 0.5 vol % to 12 vol %, preferably 4 vol %;
  a xylitol content from 0.1 vol % to 30 vol %, preferably 10 vol %;

additional components that can properly complete the formula.

Disinfection Method

Another objective of this invention is the provision of a disinfection method, especially for lasting disinfection of synthetic fibers, synthetic surfaces, metallic surfaces, composite surfaces and the like.

The method according to the invention comprises the following steps:
a) washing the surface to be disinfected with running water;
b) washing the surface to be disinfected with saline (optional);
c) immersing the surface to be disinfected in the disinfection composition and/or applying the disinfection composition on the surface to be disinfected;
d) allowing the action of the disinfection composition during 5 to 15 minutes, preferably 10 minutes;
e) emerging the surface to be disinfected in the disinfection composition (considering the immersion of step 'c');
f) washing the surface to be disinfected with running water; and
g) washing the surface to be disinfected with saline (optional).

Disinfection Protocol for Toothbrushes

Another objective of this invention is the provision of a disinfection protocol, notably for the lasting disinfection of bristles of toothbrushes.

posite surfaces and the like, comprising a disinfection composition according to the invention.

In a preferred embodiment of the invention, the product according to the invention is a liquid or fluid for immersion.

In another preferred embodiment of the invention, the product according to the invention is an effervescent material (pill, tablet, powder or similar) or aerosol, or a misting or infusion fluid, or vapor, or any other form that is suitable for application to surfaces.

Tests/Results

In order to test the effectiveness of the disinfection composition according to the invention and its extended action, numerous laboratory tests were conducted, two of which have their results briefly presented below.

One of the tests performed was the verification of the minimum extended action time of the disinfection composition according to the invention, by dipping toothbrushes infected with *Escherichia coli* and *Pseudomonas aeruginosa* separately in a vessel containing the composition according to the invention.

Contamination of two separate solutions with each of the bacteria was performed, the bristles of a toothbrush being, then, immersed in said contaminated solutions, contaminating them completely.

Two toothbrushes were infected, each with one of the types of bacteria. Bacteria continued to be inoculated daily and the toothbrushes were kept in their respective fluids kept in an oven at 37° C.

Said contaminated brushes were then immersed in a disinfection composition according to the invention. The following table (Table 1) shows the result of the presence of bacteria in the infected brushes immersed in those test liquids, for 7 (seven) days, for each bacteria.

TABLE 1

| | 7 days laboratory test | | | | | | |
|---|---|---|---|---|---|---|---|
| | DAY 1 | DAY 2 | DAY 3 | DAY 4 | DAY 5 | DAY 6 | DAY 7 |
| | Bacterium: *Escherichia Coli* | | | | | | |
| TOOTHBRUSH 1 | NEGATIVE | NEGATIVE | NEGATIVE | NEGATIVE | NEGATIVE | NEGATIVE | NEGATIVE |
| TOOTHBRUSH 2 | NEGATIVE | NEGATIVE | NEGATIVE | NEGATIVE | NEGATIVE | NEGATIVE | NEGATIVE |
| | Bacterium: *Pseudomonas Aeruginosa* | | | | | | |
| TOOTHBRUSH 1 | NEGATIVE | NEGATIVE | NEGATIVE | NEGATIVE | NEGATIVE | NEGATIVE | NEGATIVE |
| TOOTHBRUSH 2 | NEGATIVE | NEGATIVE | NEGATIVE | NEGATIVE | NEGATIVE | NEGATIVE | NEGATIVE |

The disinfection protocol comprises the following steps:
a) washing hands;
b) performing oral hygiene with a toothbrush and a dentifrice or appropriate oral hygiene product;
c) washing the toothbrush with running water;
d) inserting a disinfection composition according to the invention into a suitable container for partial immersion of the toothbrush;
e) immersing the bristles head of the toothbrush in the disinfection composition;
f) allowing the action of the disinfection composition during 5 to 15 minutes, preferably 10 minutes or removing the toothbrush only at the time of the next oral hygiene procedure;
g) disposing said used disinfection composition after a maximum of 7 days;
h) washing the bristles of the toothbrush with running water before the next oral hygiene procedure.

Product

Another objective of this invention is the provision of a disinfection product, especially for lasting disinfection of synthetic fibers, synthetic surfaces, metallic surfaces, com- Taking into consideration Table 1 above, one concludes that the qualitatively tested disinfection composition has an extended action during at least seven days, without being replaced or replenished throughout the testing period. The composition according to the invention was successful considering the extended period criterion, even with daily inoculation of bacteria.

Another test performed was the one for efficacy of elimination of microorganisms strains added to different liquids, including the composition according to the invention, by measuring the residual content of the strains in those fluids.

The microorganism strains used are recited in the results table below (Table 2).

The disinfection liquids prepared and tested are also recited in the results table below (Table 2).

Antimicrobial activities of three liquids were analyzed, namely: (i) Purified water (reference) (ii) Solution A (1 vol % chlorhexidine, 4 vol % alkylpolyglycosides, 10 vol % xylitol and purified water qsp pH 6.0) and Solution B (5 vol % chlorhexidine, 4 vol % alkylpolyglycosides, 10 vol % xylitol and purified water qsp pH 6.0).

Methodology: inoculation of each microorganism at $10^6$ in each respective disinfection liquid, individually. Keeping it in each liquid for a disinfection action for 10 minutes. Then, the respective cultures were carried out in which there was quantitative analysis with a counting method after 48 hours in an oven.

Table 2 results, referring to residual activity, prove the effectiveness of compositions according to the invention.

TABLE 2 antimicrobial activity by contact time

| Product | Candida Inoculum $5.3 \times 10^5$ CFU | Klebsiella Inoculum $1.1 \times 10^6$ CFU | E. Coli Inoculum $5.0 \times 10^6$ CFU | Samonella Inoculum $4.6 \times 10^6$ CFU | S. Mutans Inoculum $2.1 \times 10^6$ CFU | S. aureus Inoculum $4.0 \times 10^6$ CFU | P. Aeruginosa Inoculum $4.7 \times 10^6$ CFU | Lactobacillus Inoculum $4.5 \times 10^5$ CFU | Decimal Reduction (% DR) Bacteria |
|---|---|---|---|---|---|---|---|---|---|
| Purified water | $2.2 \times 10^5$ | $6.7 \times 10^5$ | $3.4 \times 10^6$ | $2.9 \times 10^6$ | $2.1 \times 10^6$ | $4.7 \times 10^6$ | $4.0 \times 10^6$ | $2.8 \times 10^5$ | No reduction |
| Solution A | <10 | <10 | <10 | <10 | <10 | <10 | <10 | <10 | 99.99 |
| Solution B | <10 | <10 | <10 | <10 | <10 | <10 | <10 | <10 | 99.99 |

Final Considerations

As can be inferred from the description above, the composition according to the invention provides lasting disinfection of synthetic fibers, synthetic surfaces, metal surfaces, composite and similar surfaces, and the like, avoiding contamination and re-contamination of said elements.

More specifically, the composition according to the invention exhibits both combined and simultaneous antibacterial, antiseptic and deep cleaning activity with extended action (of at least seven days) especially for continuous use in toothbrush bristles, but also effective for the disinfection of other synthetic or metallic surfaces (such as, for example, oral hygiene instruments such as tongue scrapers, dental floss bow, among others), in addition to surfaces of oral devices (braces and retainers for instance), prostheses, and even hearing aids, combining minimal toxicity (to the human body) to maximum effectiveness.

The effectiveness of the composition according to the invention also extends to the complementary residues that can be found on the surfaces of objects to be disinfected, for example, fat, dentifrice debris, food debris, organic tissue, saliva, soaps, shampoos, rinses and the like, their continuous and daily use being guaranteed, without restrictions due to its non-toxic components.

In addition, there is room for a composition having a lasting action on the disinfected surfaces as above-mentioned and which can additionally be beneficial to the health of the user, in a complementary manner. Said composition containing, for instance, compounds that have anti-caries efficacy and the like, presenting antimicrobial and also dental plaque inhibiting action, thus achieving a reduction of oral diseases and halitosis, in addition to various conditions related to medical and hearing aids.

Conclusion

Those skilled in the art will easily understand that modifications can be made to the present invention without straying from the concepts exposed in the above description. These modifications are to be considered comprised by the scope of the present invention. Consequently, the particular embodiments previously described in detail are only illustrative and exemplary as well as non-restrictive with regards to the scope of the present invention, to which the full extent of the appended claims and of each and every equivalent should be given.

The invention claimed is:

1. Disinfection composition, wherein the composition comprises:
   (i) from 0.1 vol % to 20 vol % of at least one chlorhexidine-based disinfection component,
   (ii) from 0.5 vol % to 12 vol % of at least one alkylpolyglycoside-based fat and residues removal component,
   (iii) from 10 vol % to 30 vol % of at least one xylitol-based protection component, and
   (iv) additional components compatible with components i, ii and iii and having reduced or zero toxicity.

2. Disinfection composition, according to claim 1, wherein the fat and residues removal component removes comprises the removal of fat, dentifrice debris, food debris, organic tissue, saliva, soaps, shampoos, and rinses.

3. Disinfection composition, according to claim 1, wherein one of the additional components is a solution of citric acid, in which the citric acid solution content is from 0.01 vol % to 10 vol %.

4. Disinfection composition, according to claim 1, wherein one of the additional components is purified water or deionized water.

5. Disinfection composition, according to claim 1, wherein of the additional components comprise a solution of citric acid and/or purified water or deionized water and one or more additional components selected from the group consisting of pH stabilizer, preservatives, flavorings, dyes and alcohol.

6. Disinfection method for surfaces, wherein the method comprises the following steps:
   a) washing the surface to be disinfected with running water;
   b) optionally washing the surface to be disinfected with saline;
   c) immersing the surface to be disinfected in a disinfection composition and/or applying a disinfection composition on the surface to be disinfected wherein the disinfectant composition comprises:
      (i) from 0.1 vol % to 20 vol % of at least one chlorhexidine-based disinfection component,
      (ii) from 0.5 vol % to 12 vol % of at least one alkylpolyglycoside-based fat and residues removal component,
      (iii) from 10 vol % to 30 vol % of at least one xylitol-based protection component, and
      (iv) additional components compatible with components i, ii and iii and having reduced or zero toxicity,
   d) allowing the action of the disinfection composition for from 5 to 15 minutes;
   e) if immersed in step c), emerging the surface to be disinfected in the disinfection composition;
   f) washing the surface to be disinfected with running water; and g) optionally washing the surface to be disinfected with saline.

7. Disinfection method for toothbrushes comprising bristles at the head of the toothbrush according to claim 6, the method comprising:
a) washing hands;
b) performing oral hygiene with a toothbrush and a dentifrice or appropriate oral hygiene product;
c) washing the toothbrush with running water;
d) inserting the disinfection composition into a suitable container for partial immersion of the toothbrush;
e) immersing the bristles head of the toothbrush in the disinfection composition;
f) allowing the action of the disinfection composition during 5 to 15 minutes or removing the toothbrush only at the time of the next oral hygiene procedure;
g) disposing said used disinfection composition after a maximum of 7 days;
h) washing the bristles of the toothbrush with running water before the next oral hygiene procedure.

8. Disinfection product for lasting disinfection of surfaces wherein the product comprises a disinfection composition of claim 1.

9. Disinfection composition, according to claim 1, wherein the additional components one or more components selected from the group consisting of pH stabilizer, preservatives, flavorings, dyes and alcohol.

10. Disinfection method for surfaces according to claim 6 wherein, in the disinfectant composition,
the additional components (iv) comprise a solution of citric acid, in which the citric acid solution content is from 0.01 vol % to 10 vol %, and/or purified water or deionized water.

11. Disinfection method for surfaces according to claim 10 wherein the surface is the surface of a fiber.

12. Disinfection method for toothbrushes comprising bristles at the head of the toothbrush according to claim 7, wherein, in the disinfectant composition, the additional components iv) comprise a solution of citric acid, in which the citric acid solution content is from 0.01 vol % to 10 vol %, and/or purified water or deionized water.

13. Disinfection product for lasting disinfection surfaces according to claim 8, wherein, in the disinfection composition the additional components iv) comprise a solution of citric acid, in which the citric acid solution content is from 0.01 vol % to 10 vol % , and/or purified water or deionized water.

* * * * *